(12) United States Patent
McPeck et al.

(10) Patent No.: US 9,370,313 B2
(45) Date of Patent: Jun. 21, 2016

(54) DEVICE AND METHOD FOR PERFORMING ELECTROENCEPHALOGRAPY

(71) Applicants: HYDRODOT, INC., Westford, MA (US); William Principe, Ayer, MA (US)

(72) Inventors: John P. McPeck, La Canada, CA (US); Kathleen M. Principe, Ayer, MA (US)

(73) Assignee: BIO-SIGNAL GROUP CORP., Brooklyn, NY (US)

( * ) Notice: Subject to any disclaimer, the term of this patent is extended or adjusted under 35 U.S.C. 154(b) by 0 days.

(21) Appl. No.: 13/776,501

(22) Filed: Feb. 25, 2013

(65) Prior Publication Data

US 2013/0172721 A1 Jul. 4, 2013

Related U.S. Application Data

(63) Continuation of application No. 12/740,639, filed as application No. PCT/US2008/082635 on Nov. 6, 2008, now abandoned.

(60) Provisional application No. 60/985,926, filed on Nov. 6, 2007.

(51) Int. Cl.
*A61B 5/00* (2006.01)
*A61B 5/0478* (2006.01)
*A61B 5/0476* (2006.01)

(52) U.S. Cl.
CPC ............. *A61B 5/0478* (2013.01); *A61B 5/4094* (2013.01); *A61B 5/4839* (2013.01); *A61B 5/6814* (2013.01); *A61B 5/6833* (2013.01); *A61B 5/0476* (2013.01); *A61B 5/6803* (2013.01); *A61B 5/6832* (2013.01); *A61B 2560/0412* (2013.01); *A61B 2562/046* (2013.01); *A61B 2562/12* (2013.01); *A61B 2562/14* (2013.01)

(58) Field of Classification Search
CPC .. A61B 5/0478; A61B 5/0476; A61B 5/6832; A61B 5/6833; A61B 5/4064; A61B 5/6814; A61B 5/6803; A61B 2562/0209
USPC .................................................. 600/544–545
See application file for complete search history.

(56) References Cited

U.S. PATENT DOCUMENTS

| | | | |
|---|---|---|---|
| 4,418,697 A | 12/1983 | Tama | |
| 5,479,934 A * | 1/1996 | Imran | 600/544 |
| 6,301,493 B1 * | 10/2001 | Marro et al. | 600/383 |
| 6,510,340 B1 * | 1/2003 | Jordan | 600/544 |
| 6,921,574 B2 | 7/2005 | Cinelli et al. | |
| 7,206,630 B1 | 4/2007 | Tarler | |

(Continued)

*Primary Examiner* — Patricia Mallari
*Assistant Examiner* — Karen Toth
(74) *Attorney, Agent, or Firm* — Nathan S. Smith; Mark I. Bentley; McDermott Will & Emery LLP (57) ABSTRACT

A device 10 for performing electroencephalography on a patient, the device comprising a sagittal portion 14 comprising: a forehead anchor 44 comprising two forehead anchor arms, a first forehead anchor arm 46 and an opposing second forehead anchor arm 48; a neck anchor 54 comprising two neck anchor arms, a first neck anchor arm 56 and an opposing second neck anchor arm 58; a midsection 52 between the forehead anchor and the neck anchor; and a plurality of imbedded electrodes 20 within the forehead anchor, and the midsection. The device further comprises: a coronal portion 12 comprising a plurality of imbedded electrodes; and electrical connectors 22 for electrically connecting the imbedded electrodes in the sagittal portion and the coronal portion to an electroencephalograph.

10 Claims, 6 Drawing Sheets

(56) References Cited

U.S. PATENT DOCUMENTS

| | | |
|---|---|---|
| 7,495,055 B2 * | 2/2009 | Soerens et al. ............. 524/588 |
| 2002/0183605 A1 | 12/2002 | Devlin et al. |
| 2004/0073127 A1 | 4/2004 | Istvan et al. |
| 2005/0245801 A9 | 11/2005 | Munro et al. |
| 2005/0251003 A1 * | 11/2005 | Istvan et al. ............. 600/393 |
| 2007/0225585 A1 | 9/2007 | Washbon et al. |
| 2008/0275327 A1 | 11/2008 | Faarbaek et al. |
| 2010/0073615 A1 | 3/2010 | Yaguchi et al. |
| 2010/0274152 A1 * | 10/2010 | McPeck et al. ............. 600/544 |
| 2012/0108920 A1 | 5/2012 | Bly et al. |

* cited by examiner

DEVICE AND METHOD FOR PERFORMING ELECTROENCEPHALOGRAPY

CROSS REFERENCE TO RELATED APPLICATIONS

The present application is a continuation of U.S. patent application Ser. No. 12/740,639 titled "Device and Method for Performing Electroencephalography," filed Apr. 29, 2010 which is a national stage of International Patent Application No. PCT/US2008/082635 titled "Device and Method for Performing Electroencephalography," filed Nov. 6, 2008, which claims the benefit of U.S. Provisional Patent Application No. 60/985,926 titled "Device and Method for Performing Electroencephalography," filed on Nov. 6, 2007, the contents of which are incorporated herein by reference in their entirety.

BACKGROUND

Electroencephalography is a technique for measuring the electrical activity of the brain by recording the electrical activity from electrodes placed on the scalp. The graph produced by electroencephalography is called an electroencephalogram (EEG).

Electroencephalography has a number of advantages over other diagnostic techniques, such as magnetic resonance imaging, in that electroencephalography records the electrical activity of the brain and does not require the patient to remain still for extended periods. Electroencephalography is generally performed by placing electrodes on the scalp using a conductive gel or paste, where each electrode is attached to an individual wire which isolates the activity at the position of the electrode. The names and locations of the electrodes are usually specified using the International 10-20 system for consistency between institutions, where 21 electrodes are used in testing an adult. A ground electrode or a ground electrode and a reference electrode are also generally used in testing.

There are a number of potentially treatable conditions which electroencephalography can diagnose through characteristic electroencephalogram patterns. Among these conditions are non-convulsive status epilepticus (NCSE), seizure and stroke. It is difficult to diagnose brain injuries such as NCSE and strokes in many patients, particularly those who have altered mental status or who are comatose without performing electroenchalography.

Disadvantageously, however, specially trained technicians are often not available to apply electroencephalography electrodes so that electroencephalography can be performed in every location and at all times. Therefore, electroencephalography as a diagnostic technique is underutilized, such as in the emergency room (ER), Intensive Care Unit (ICU), operating room (OR), at accident scenes and in a battlefield situation. Further, routine electroencephalography as a part of a primary medical examination is generally not performed, in part because of the difficulty of placing the electrodes properly. Additionally, currently used electroencephalography devices are costly to produce, and are therefore cleaned between uses so that the devices can be reused on other patients. The cleaning and disinfecting process is time consuming.

Therefore, there is a need for a device for performing electroencephalography which is not associated with the disadvantages of currently used devices.

SUMMARY

According to one embodiment of the present invention, there is provided a device for performing electroencephalography on a patient. The device comprises a sagittal portion comprising: i) a forehead anchor comprising two arms, a first forehead anchor arm and an opposing second forehead anchor arm; ii) a neck anchor comprising two arms, a first neck anchor arm and an opposing second neck anchor arm; iii) a midsection between the forehead anchor and the neck anchor; and iv) a plurality of imbedded electrodes within the forehead anchor, and the midsection. The device further comprises: a coronal portion comprising a plurality of imbedded electrodes; and electrical connectors for electrically connecting the imbedded electrodes in the sagittal portion and the coronal portion to an electroencephalograph.

In a preferred embodiment, the sagittal portion and the coronal portion comprise a contact surface, and the contact surface comprises a silicone based adhesive for reversibly attaching the device to the patient. In another preferred embodiment, the sagittal portion or the coronal portion or both the sagittal portion and the coronal portion comprise a release film covering the contact surface. In another embodiment, the forehead anchor further comprises a third forehead anchor arm between the first forehead anchor arm and the second forehead anchor arm. In another embodiment, the neck anchor further comprises a third neck anchor arm between the first neck anchor arm and the second neck anchor arm. In another embodiment, the imbedded electrodes in the forehead anchor consist of electrodes positioned at positions $F_7$, $F_{P1}$, $F_{P2}$, $F_8$ of the International Standard 10-20 System for electrode placement. In another embodiment, the imbedded electrodes in the midsection consist of electrodes positioned at positions $F_Z$, $C_Z$, $P_Z$, $O_1$ and $O_2$ of the International Standard 10-20 System for electrode placement. In a preferred embodiment, the forehead anchor further comprises a reference electrode or a ground electrode or a reference electrode and a ground electrode. In a preferred embodiment, a plurality of sponges are attached to the embedded electrodes. In a further preferred embodiment, one or more than one of the plurality of sponges contains a conductive gel.

According to another embodiment of the present invention, there is provided a device for performing electroencephalography on a patient. The device comprises a coronal portion comprising: i) a first ear anchor comprising a front arm and a rear arm; ii) a second ear anchor comprising a front arm and a rear arm; iii) a midsection between the first ear anchor and the second ear anchor; and iv) a plurality of imbedded electrodes within the first ear anchor, the midsection and the second ear anchor. The device further comprises a sagittal portion comprising a plurality of imbedded electrodes; and electrical connectors for electrically connecting the imbedded electrodes in the sagittal portion and the coronal portion to an electroencephalograph.

In a preferred embodiment, the sagittal portion and the coronal portion comprise a contact surface, and the contact surface comprises a silicone based adhesive for reversibly attaching the device to the patient. In another preferred embodiment, the sagittal portion or the coronal portion or both the sagittal portion and the coronal portion comprise a release film covering the contact surface. In another embodiment, the imbedded electrode in the first ear anchor is positioned at position $A_1$ of the International Standard 10-20 System for electrode placement. In another embodiment, the imbedded electrode in the second ear anchor is positioned at position $A_2$ of the International Standard 10-20 System for electrode placement. In another embodiment, the imbedded electrodes in the midsection consist of electrodes positioned at positions $T_3$, $C_3$, $C_4$, and $T_4$ of the International Standard 10-20 System for electrode placement. In a preferred embodiment, a plurality of sponges are attached to the embedded electrodes. In a further preferred embodiment, one or more than one of the plurality of sponges contains a conductive gel.

According to another embodiment of the present invention there is provided a device for performing electroencephalography on a patient, the device comprising: a sagittal portion comprising: i) a forehead anchor comprising two arms, a first forehead anchor arm and an opposing second forehead anchor arm; ii) a neck anchor comprising two arms, a first neck anchor arm and an opposing second neck anchor arm; iii) a midsection between the forehead anchor and the neck anchor; and iv) a plurality of imbedded electrodes within the forehead anchor, and the midsection. The device further comprises a coronal portion comprising: i) a first ear anchor comprising a front arm and a rear arm; ii) a second ear anchor comprising a front arm and a rear arm; iii) a midsection between the first ear anchor and the second ear anchor; and iv) a plurality of imbedded electrodes within the first ear anchor, the midsection and the second ear anchor. The device further comprises electrical connectors for electrically connecting the imbedded electrodes in the sagittal portion and the coronal portion to an electroencephalograph.

In a preferred embodiment, the sagittal portion and the coronal portion comprise a contact surface, and the contact surface comprises a silicone based adhesive for reversibly attaching the device to the patient. In another preferred embodiment, the sagittal portion or the coronal portion or both the sagittal portion and the coronal portion comprise a release film covering the contact surface. In a preferred embodiment, a plurality of sponges are attached to the embedded electrodes. In a further preferred embodiment, one or more than one of the plurality of sponges contains a conductive gel.

In another embodiment, the forehead anchor further comprises a third forehead anchor arm between the first forehead anchor arm and the second forehead anchor arm. In another embodiment, the neck anchor further comprises a third neck anchor arm between the first neck anchor arm and the second neck anchor arm. In another embodiment, the imbedded electrodes in the forehead anchor consist of electrodes positioned at positions $F_7$, $F_{P1}$, $F_{P2}$, $F_8$ of the International Standard 10-20 System for electrode placement. In another embodiment, the imbedded electrodes in the midsection consist of electrodes positioned at positions $F_Z$, $C_Z$, $P_Z$, $O_1$ and $O_2$ of the International Standard 10-20 System for electrode placement. In a preferred embodiment, the forehead anchor further comprises a reference electrode or a ground electrode or a reference electrode and a ground electrode. In another embodiment, the imbedded electrode in the first ear anchor is positioned at position $A_1$ of the International Standard 10-20 System for electrode placement. In another embodiment, the imbedded electrode in the second ear anchor is positioned at position $A_2$ of the International Standard 10-20 System for electrode placement. In another embodiment, the imbedded electrodes in the midsection consist of electrodes positioned at positions $T_3$, $C_3$, $C_4$, and $T_4$ of the International Standard 10-20 System for electrode placement.

According to another embodiment of the present invention there is provided a device for performing electroencephalography on a patient, the device comprising: a sagittal portion comprising a plurality of imbedded electrodes; a coronal portion comprising a plurality of imbedded electrodes; and electrical connectors for electrically connecting the imbedded electrodes in the sagittal portion and the coronal portion to an electroencephalograph. The sagittal portion and the coronal portion each comprise a contact surface that comprises a silicone based adhesive for reversibly attaching the device to the patient. In a preferred embodiment, the sagittal portion or the coronal portion or both the sagittal portion and the coronal portion comprise a release film covering the contact surface.

According to another embodiment of the present invention there is provided a method of performing electroencephalography on a patient. The method comprises: providing a device for performing electroencephalography on the patient, the device comprising: a sagittal portion and a coronal portion, each of the sagittal portion and the coronal portion comprising a plurality of imbedded electrodes; and electrical connectors for electrically connecting the imbedded electrodes in the sagittal portion and the coronal portion to an electroencephalograph.

The method further comprises affixing the device to the patient; and producing an electroencephalogram. In a preferred embodiment, the device comprises a liner, and the method further comprises removing the liner before affixing the device. In another preferred embodiment, the device comprises a stabilizing strip, and affixing the device to the patient further comprises affixing the stabilizing strip to the sagittal portion or the coronal portion or the sagittal portion and the coronal portion, and to the patient. In an embodiment, affixing the device to the patient further comprises affixing the forehead anchor to the forehead of the patient, affixing the midsection along a sagittal midline of the head of the patient and affixing the neck anchor to the base of the skull proximal the neck of the patient. In another embodiment, affixing the device to the patient further comprises affixing the first ear anchor around the left ear of the patient and affixing the second ear anchor around the right ear of the patient.

According to another embodiment of the present invention there is provided a method of diagnosing a neurologic condition or disease. The method comprises: selecting a patient potentially with the neurologic condition or disease. The method further comprises: providing a device for performing electroencephalography on the patient, the device comprising: a sagittal portion and a coronal portion, each of the sagittal portion and the coronal portion comprising a plurality of imbedded electrodes; and electrical connectors for electrically connecting the imbedded electrodes in the sagittal portion and the coronal portion to an electroencephalograph. The method further comprises: affixing the device to the patient; and producing an electroencephalogram. In a preferred embodiment, the method further comprises diagnosing the neurologic condition or disease by interpreting the electroencephalogram. In another embodiment, the method further comprises treating the neurologic condition or disease that is diagnosed. In an embodiment, the neurologic condition or disease is non-convulsive status epilepticus or an epileptic seizure or a stroke.

DRAWINGS

These and other features, aspects and advantages of the present invention will become better understood with regard to the following description, appended claims, and accompanying drawings where:

DESCRIPTION

According to one embodiment of the present invention, there is provided a device for performing electroencephalography. Preferably, the electroencephalography device comprises an EEG headpiece made with inexpensive materials and designed to be disposable. The electroencephalography device comprises a self-adhesive backing and integrated circuitry connected to self-prepping, pre-gelled imbedded electrodes. Preferably, the electroencephalography device utilizes a modified 10-20 electrode positioning system having fewer electrodes than the standard 10-20 placement for simple recording, but with sufficient EEG locations to record information over critical brain locations.

The device provides sufficient EEG channels to determine if the patient's brain activity is normal or abnormal and to then quickly treat the patient based on the interpretation of the EEG. The electroencephalography device can be easily applied by technicians or other medical personnel with minimal training, allowing the electroencephalography device to be used in situations where electroencephalography is currently difficult to perform because of the complex placement of the electrodes, such as in the emergency room (ER), Intensive Care Unit (ICU), operating room (OR), at accident scenes and in a battlefield situation. Additionally, the electroencephalography device can be used to record cortical evoked potentials and EEG recordings during sleep studies, or other studies as will be understood by those with skill in the art with reference to this disclosure.

According to another embodiment of the present invention, there is provided a method for performing electroencephalography. In a preferred embodiment, the method comprises providing an electroencephalography device according to the present invention, and recording an EEG.

According to another embodiment of the present invention, there is provided a kit for performing electroencephalography. In one embodiment, the kit comprises an electroencephalography device according to the present invention. The device, method and kit will now be disclosed in detail.

As used herein, except where the context requires otherwise, the term "comprise" and variations of the term, such as "comprising," "comprises" and "comprised" are not intended to exclude other additives, components, integers or steps.

As used in this disclosure, two elements of an electroencephalography device are "integral" or "integrated" if they are joined together in a manner that does not allow separation of the two elements from one another by the user of the device without diminishing or destroying the function one or both of the two elements.

All dimensions specified in this disclosure are by way of example only and are not intended to be limiting. Further, the proportions shown in these Figures are not necessarily to scale. As will be understood by those with skill in the art with reference to this disclosure, the actual dimensions of any electroencephalography device or part of an electroencephalography device disclosed in this disclosure will be determined by its intended use, including being sized appropriately for use on infants and children.

The electroencephalography device of the present invention and its component parts comprise any suitable material for the intended purpose of the electroencephalography device, as will be understood by those with skill in the art with reference to this disclosure. Reference to specific materials in this disclosure are by way of example only.

The electroencephalography device of the present invention and its component parts can be constructed according to standard techniques, as will be understood by those with skill in the art with reference to this disclosure.

Figure 1:
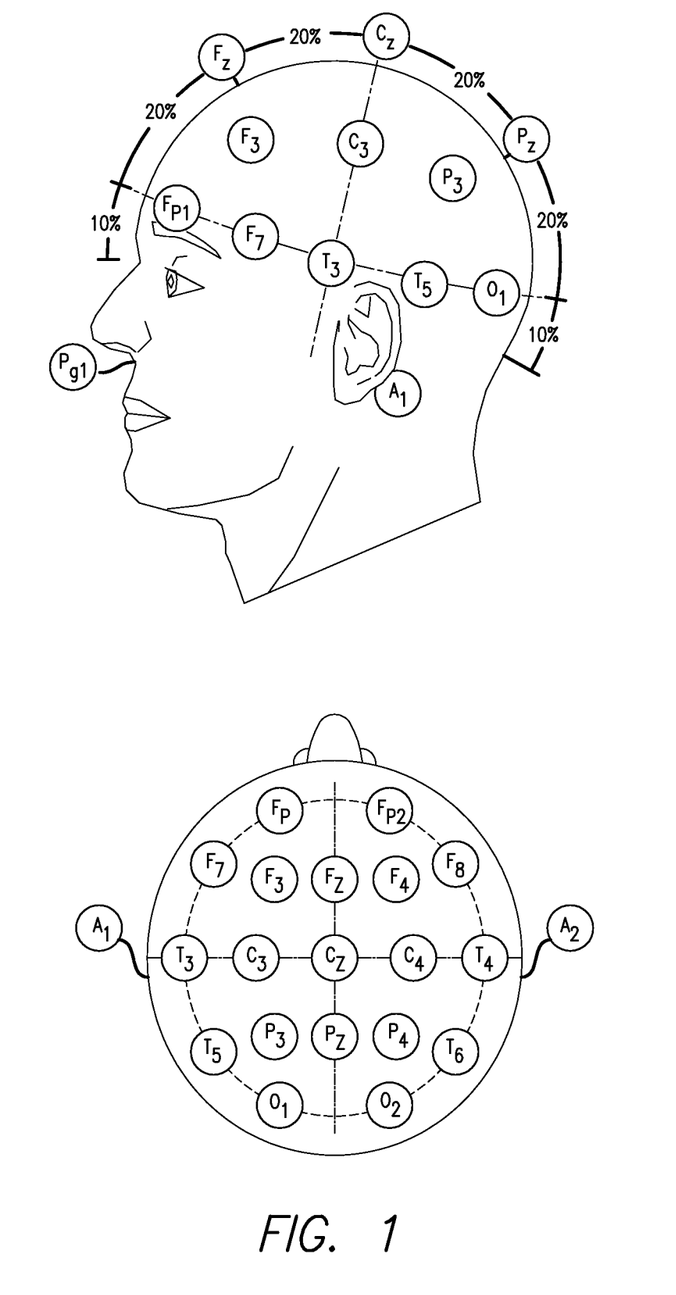
FIG. 1 is a drawing showing the standard placement of electrodes in the standard 10-20 system for EEG electrode placement.

Referring now to FIG. 1, a drawing showing the standard placement of electrodes in the standard 10-20 system for EEG electrode placement. As can be seen, in the standard 10-20 system for electrode placement, there are 21 electrodes placed at positions $F_{P1}$, $F_{P2}$, $F_7$, $F_3$, $F_Z$, $F_4$, $F_8$, $A_1$, $T_3$, $C_3$, $C_Z$, $C_4$, $T_4$, $A_2$, $T_5$, $P_3$, $P_Z$, $P_4$, $T_6$, $O_1$ and $O_2$ (given from front to back, left side to right side). In a preferred embodiment of the present invention the electrodes are placed on $F_{P1}$, $F_{P2}$, $F_7$, $F_Z$, $F_8$, $A_1$, $T_3$, $C_3$, $C_Z$, $C_4$, $T_4$, $A_2$, $P_Z$, $O_1$ and $O_2$. Additionally, the electroencephalography device according to an embodiment can have one or more of a reference electrode and a ground electrode. These electrodes are typically placed at locations $F_{PZ}$ and $AF_Z$ on a standard 10-10 system for electrode placement (not shown).

Figure 2:
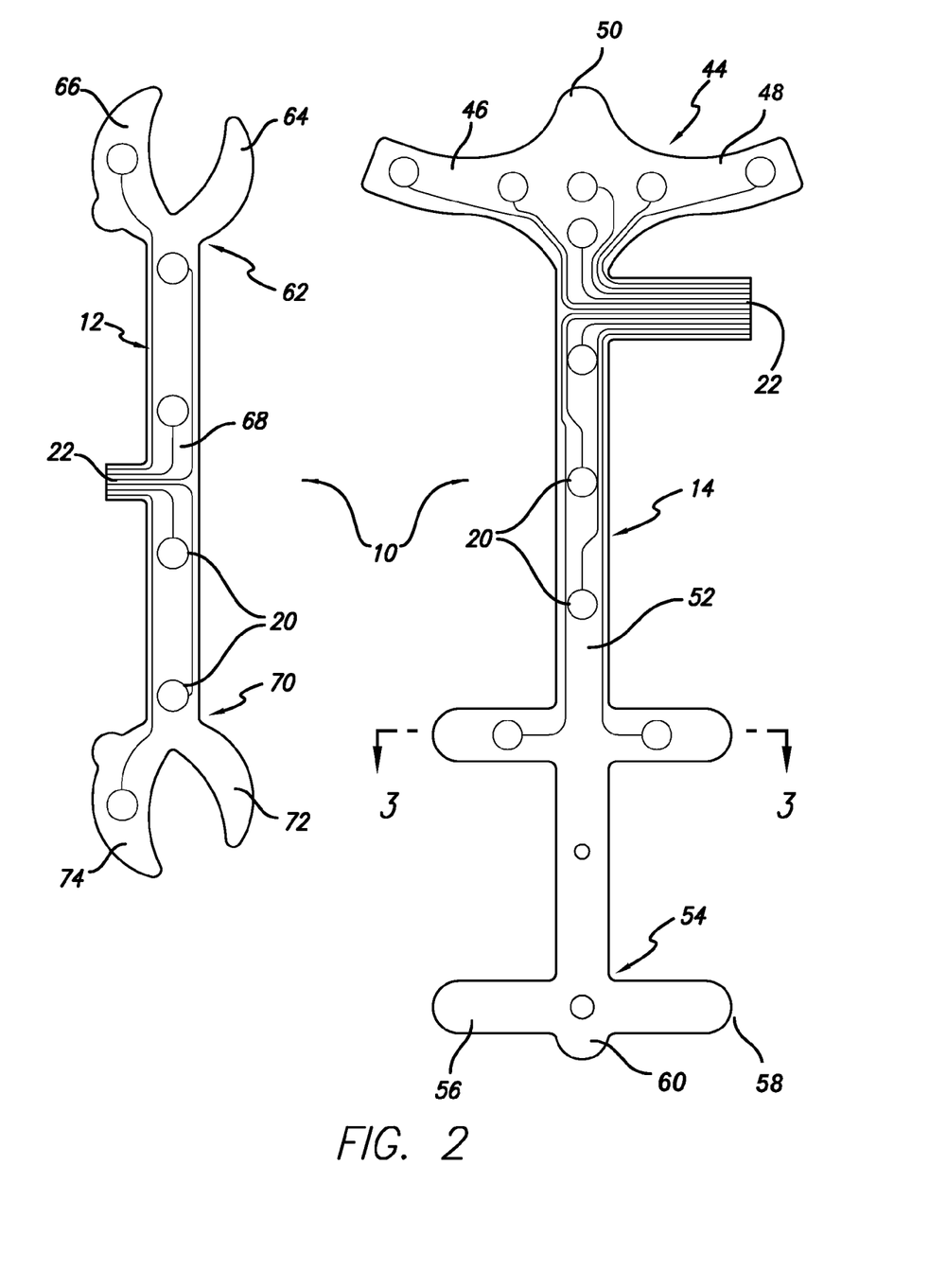
FIG. 2 is a schematic view of a device for performing electroencephalography according to an embodiment of the present invention.

In one embodiment, the present invention is an electroencephalography device for performing electroencephalography. Referring now to FIG. 2, there is shown a schematic view of an electroencephalography device for performing electroencephalography according to the present invention. As can be seen, the electroencephalography device 10 comprises two portions, a coronal portion 12 depicted on the left side of FIG. 1, and a sagittal portion 14 depicted on the right side of FIG. 1. In another embodiment of the present invention, the coronal portion 12 and the sagittal portion 14 of the electroencephalography device 10 are integrally connected at or near their axial midpoints.

Figure 3:
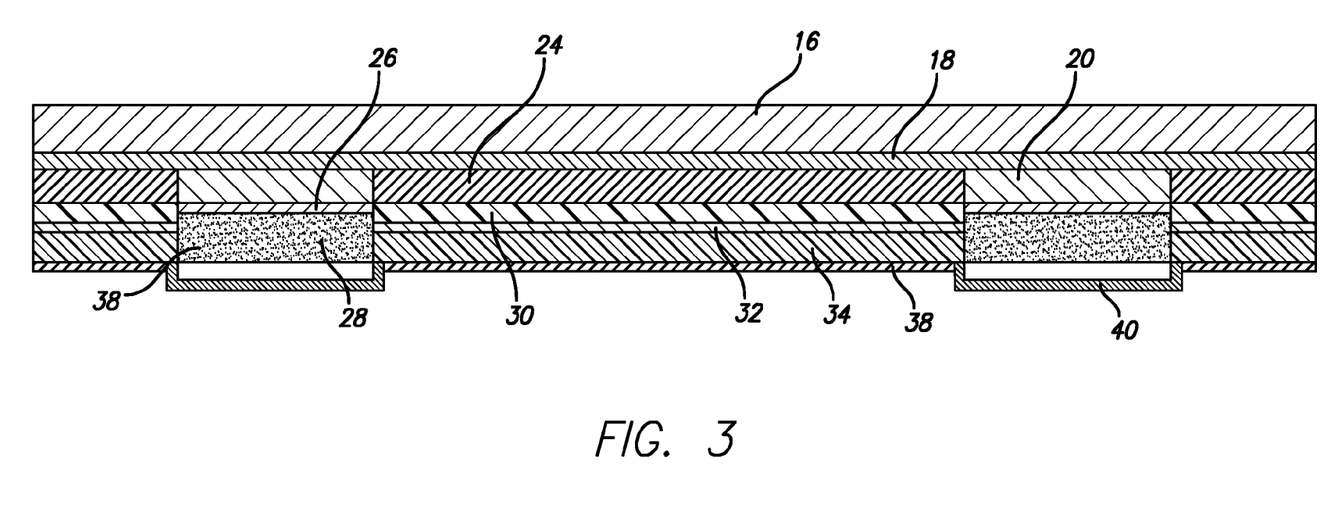
FIG. 3 is a cross sectional view of the device of FIG. 2 taken along line 3-3.

The various components of the electroencephalography device 10 according to an embodiment of the present invention will now be described in more detail with reference to FIG. 2 and FIG. 3. The device 10 has a base layer 16. Preferably, the base layer 16 is a plastic, such as for example a polyester material having a thickness of between about 3 and about 5 mil. Conductive silver circuitry 18 is placed onto the outer layer 16, such as by printing. A plurality of electrodes 20 are placed at specific locations in contact with the silver circuitry 18, such as by printing. Preferably, the electrodes 20 are silver/silver chloride. The silver circuitry 18 leads from each electrode 20 and terminates in connectors 22. The connectors 22 are configured to mate with corresponding connectors (not shown) on a reusable EEG interface cable with 10-20 labeled DIN connectors that plug into any standard EEG recording system head box with standard DIN inputs. Those of skill in the art will recognize that other conductive materials may be used for the circuitry 18 and the electrodes 20.

A dielectric layer 24 covers the silvers circuitry 18 and outer layer 16 to insulate the circuitry. Preferably, the dielectric layer 24 is a polymer composition, has a thickness of between about 0.5 and about 2.0 mil, and is printed over the silver circuitry 18 and the outer layer 16. In a preferred embodiment of the present invention, the dielectric layer is 5018 UV Curable Dielectric sold by DuPont Microcircuit Materials, Research Triangle Park, N.C. USA. A sponge adhesive 26 is placed in the area around the electrodes 20. Sponges 28 are adhered to the sponge adhesive 26, thereby imbedding the sponges 28 in contact with the electrodes 20.

An acrylic adhesive layer 30 covers the dielectric layer 24. The acrylic adhesive layer 30 has a thickness of between about 1 and about 3 mil. A film layer 32 covers the acrylic adhesive 30. In an embodiment the film layer 32 is a polyester material having a thickness between about 0.5 and about 1.5 mil. A silicone based adhesive layer 34 covers the film layer 28. Preferably, the silicone based adhesive layer 34 has a thickness of between about 4 and about 8 mil, and more preferably between about 5 and about 7 mil. The silicone based adhesive layer functions as a contact surface where the electroencephalography device contacts the head of a patient. A release film 36 covers the silicone based adhesive layer 34.

As used herein the term "silicone based adhesive" comprises adhesives made from polydimethylsiloxanes (PDMS). Some methyl groups in the polydimethylsiloxanes can be substituted by other organic groups or atoms, for example hydrogen, hydroxyl, vinyl, polyethylene oxide, methoxy and fluoride groups, to modify the properties of the adhesive. In a preferred embodiment of the present invention, the silicone based adhesive is the silicone based adhesive found in BIOFLEX RX1268S, sold by Scapa North America, Windsor, Conn. USA. In an additional embodiment of the present invention, the silicone based adhesive layer 34 covers the dielectric layer 24 with no acrylic adhesive layer 30 or film layer 32.

A conductive gel 38, such as KCl gel or hyrdrogel, is soaked into the sponges 28. The device 10 is placed into a tray (not shown) having a plurality of wells 40. The pre-soaked sponges sit within the wells 40 to protect the fluid contained therein. In an additional embodiment, the wells can be filled with additional conductive gel. Alternatively, the release film 36 has wells 40 that extend over the pre-soaked sponges 34.

In one embodiment, the device 10 is manufactured from two separate pieces. A first piece with the base layer 16, silver circuitry 18, electrodes 20, dielectric layer 24 and sponge adhesive 26 is attached to a second piece having the acrylic adhesive 30, film layer 32, silicone adhesive layer 34 and release film 36. The second piece may be a commercially available double coated co-polyester film with a release paper (not shown) over the acrylic adhesive 30. Prior to attachment with the first piece, the second piece is cut, such as with a laser, to make holes in the second layer corresponding to the electrodes 20 and sponge adhesive 26 in the first piece, the release paper removed and the acrylic adhesive 30 coupled to the dielectric layer 24. Following attachment of the second piece, the sponges 28 are attached to the sponge adhesive 26. In a preferred embodiment of the present invention, the double coated co-polyester film is BIOFLEX RX1268S, sold by Scapa North America, Windsor, Conn. USA.

The sagittal portion 14 comprises a forehead anchor 44 with an array of pre-gelled electrodes, where the electrodes are positioned across the forehead in predetermined International 10-20 System locations, such as for example $F_{P1}$, $F_{P2}$, $F_7$, $F_8$, a Reference® electrode and a ground electrode (G). The forehead anchor has a first forehead anchor arm 46 and a second forehead anchor arm 48. Preferably, the first forehead anchor arm 46 and the second forehead anchor arm 48 extend in opposing directions. In an embodiment, the forehead anchor 44 also has a third forehead anchor arm 50 located between the first forehead anchor arm 46 and the second forehead anchor arm 48.

A midsection 52 extends from the forehead anchor 44. The midsection 52 has an anterior to posterior array of pre-gelled electrodes positioned in predetermined 10-20 locations, such as for example, $F_Z$, $C_Z$, $P_Z$, $O_1$ and $O_2$. The midsection terminates in a neck anchor 54 at the base of the skull (shown at the bottom of FIG. 2).

The neck anchor 54 has a first neck anchor arm 56 and a neck anchor second arm 58. Preferably, the first neck anchor arm 56 and the second neck anchor arm 58 extend in opposing directions perpendicular to the midsection 52. In an embodiment, the neck anchor 54 also has a third neck anchor arm 60 located between the first neck anchor arm 56 and the second neck anchor arm 58.

The coronal portion 12 comprises an array of pre-gelled electrodes positioned in predetermined 10-20 locations, such as for example $A_1$, $T_3$, $C_3$, $C_4$, $T_4$ and $A_2$ (shown in FIG. 1 and FIG. 2). When placed on the patient the electrodes are located transversely along the central coronal plane from the predetermined 10-20 location beginning at $A_1$ on the left side of the head behind the left ear on the mastoid, continuing on the left side with pre-gelled electrode locations $T_3$ and $C_3$, transecting location $C_Z$ of the International 10-20 System and continuing on the right side with pre-gelled electrode locations $C_4$ and $T_4$ and terminating at predetermined 10-20 location $A_2$ on the right side of the head behind the right ear on the mastoid.

The coronal portion 12 comprises a first ear anchor 62, having a front arm 64 configured to be placed around and in front of the left ear of the patient and a rear arm 66 configured to be placed around and behind the left ear of the patient. An electrode for 10-20 location $A_1$ is located on the rear arm 66. A midsection 68 extends from the first ear anchor 62. The midsection 68 terminates in a second ear anchor 70. The second ear anchor has a front arm 72 configured to be placed around and in front of the right ear of the patient and a rear arm 74 configured to be placed around and behind the right ear of the patient. An electrode for 10-20 location $A_2$ is located on the rear arm 74.

Figure 4:
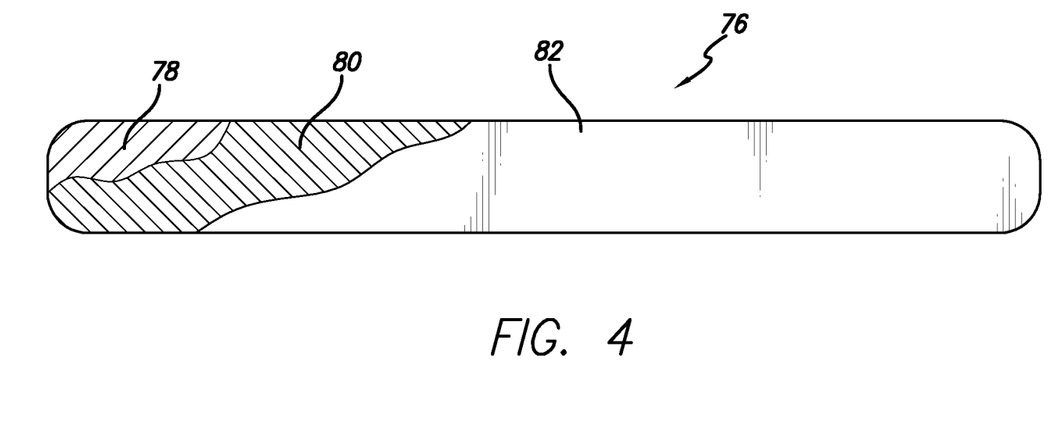
FIG. 4 is a partial cut away lateral perspective view of a stabilizing strip for use with the device of FIG. 2 according to an embodiment of the present invention.

In an additional embodiment with reference to FIG. 4, the electroencephalography device 10 additionally comprises one or more than one adhesive coated stabilizing strip 76 to attach the midsection 52 of the sagittal portion 14 proximal to the electrodes over 10-20 locations $O_1$ and $O_2$ to the mastoid bones of the patient. Additionally, the stabilizing strip 76 can attach the forehead anchor 44 proximal to the electrodes over 10-20 locations $F_7$ and $F_8$ to the head of the patient. In an embodiment, the stabilizing strip has a base layer 82, which may be a polyester film, covered with a silicone based adhesive 84. In an embodiment, a release film 86 covers the silicone adhesive 86.

Figure 5:
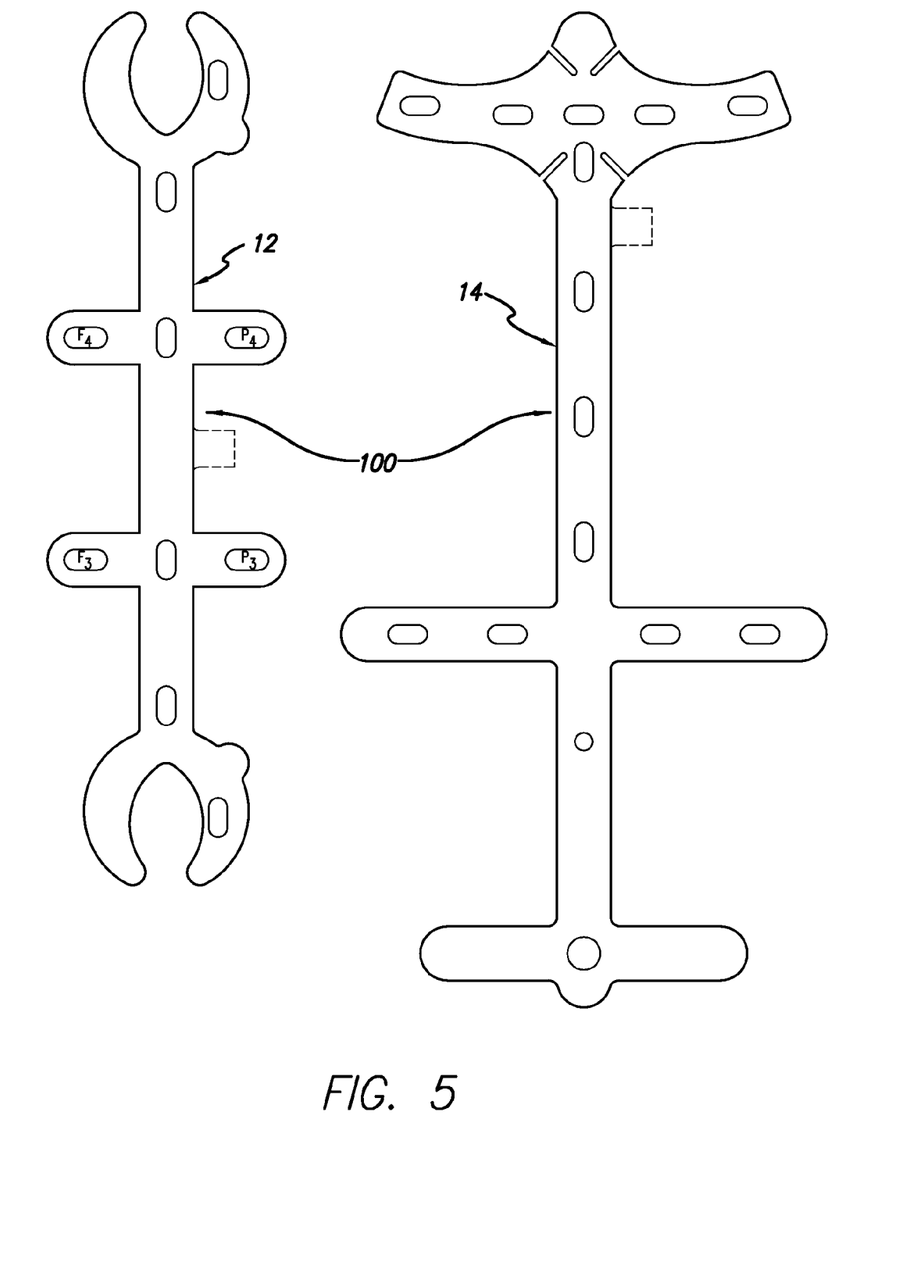
FIG. 5 is a schematic view of a device for performing electroencephalography according to an additional embodiment of the present invention.

In an additional embodiment with reference to FIG. 5, an electroencephalography device 100 is configured to cover all of the 10-20 electrode locations. The structure of this embodiment is similar to the embodiment shown in FIG. 2. However, the midsection 52 of the sagittal portion 14 is configured to provide electrodes at 10-20 locations $T_5$ and $T_6$. Stabilizing strips 76 can be used to attach the midsection of 52 of the sagittal portion 14 proximal to the electrodes at 10-20 locations $T_5$ and $T_6$ to the mastoid bones of the patient. Additionally, the midsection 68 of the coronal portion 12 is configured to provide electrodes at 10-20 locations $F_3$, $F_4$, $P_3$ and $P_4$. Stabilizing strips 76 can be used to attach the midsection 68 of the coronal portion 12 proximal to the electrodes at 10-20 locations $F_3$, $F_4$, $P_3$ and $P_4$ to the sagittal strip or to the head of a wearer.

In additional embodiments, the electroencephalography device is configured with different combinations of electrodes for specific usages. For example, when configured for use in a sleep study, the electroencephalography device may be configured so that the coronal portion has electrodes at 10-20 locations $A_1$, $C_4$, $C_3$ and $A_2$, and the sagittal portion has reference and ground electrodes and electrodes at 10-20 locations $F_3$, $F_4$, $C_Z$, $O_1$, $O_2$. Additionally, as will be understood by one of skill in the art, the electroencephalography device may be configured to have electrodes at locations other than 10-20 locations. For example, when configured for use in an evoked potential study, the sagittal portion may also be configured to have an electrode at location $O_Z$ of the 10-10 system for EEG electrode placement.

Preferably, the electroencephalography device is a disposable EEG headpiece, that is, the electroencephalography device is inexpensive enough to manufacture that it can be considered disposable in routine use. Depending on the electroencephalography requirements of a given patient, the coronal portion 12 and the sagittal portion 14 can be used separately or in combination.

Kit

Figure 6:
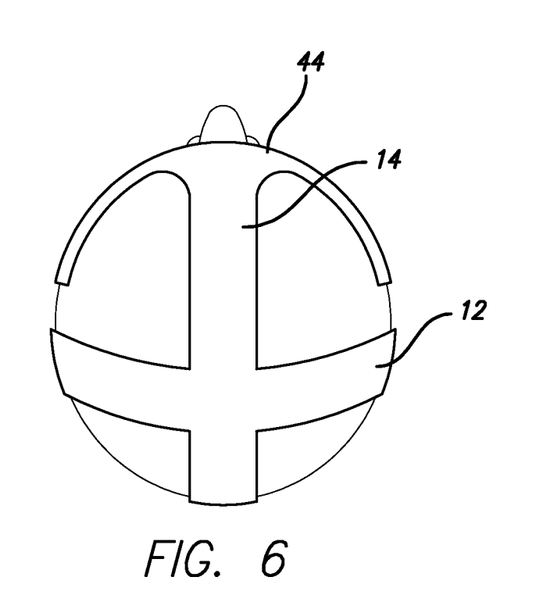
FIG. 6 is a top perspective view showing placement of the electroencephalography device of FIG. 2 on the head of a patient according to an embodiment of the present invention.
Figure 7:
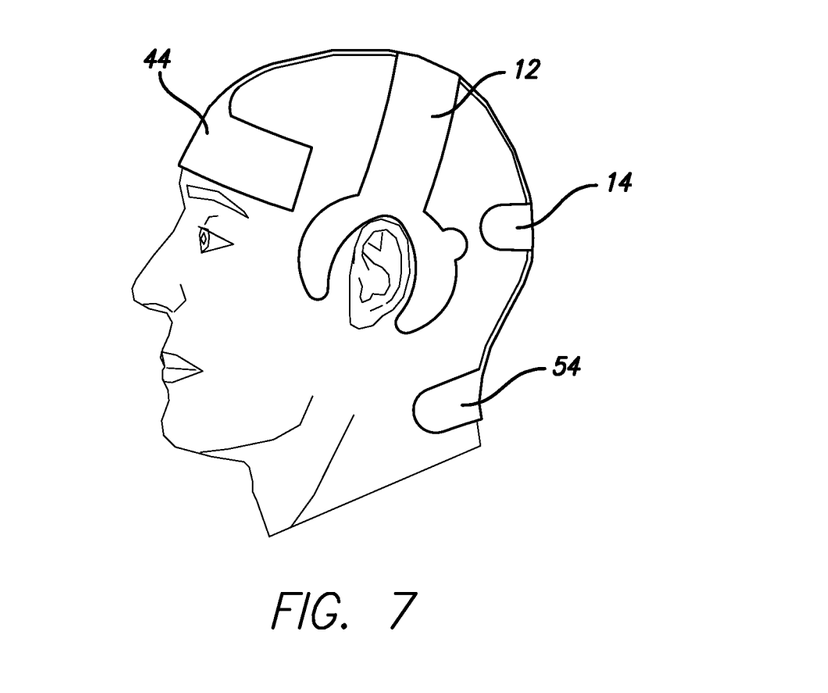
FIG. 7 is a lateral perspective view showing placement of the electroencephalography device of FIG. 2 on the head of a patient according to an embodiment of the present invention.

According to another embodiment of the present invention, there is provided a method for performing electroencephalography. In a preferred embodiment, the method comprises providing an electroencephalography device according to the present invention. An example of the method will now be disclosed with reference to FIG. 6 and FIG. 7. FIG. 6 and FIG. 7, are respectively, a top perspective view showing placement of the electroencephalography device of FIG. 2 on the head of a patient (FIG. 6); and a lateral perspective view showing placement of the electroencephalography device of FIG. 2 on the head of a patient (FIG. 7). As used in this disclosure, except where the context requires otherwise, the method steps disclosed are not intended to be limiting nor are they intended to indicate that each step is essential to the method or that each step must occur in the order disclosed.

First, a suitable patient is selected. In a preferred embodiment, the patient is known to have a disease of the brain, or is suspected of having a disease of the brain that can be identified or quantified by electroencephalography. In one embodiment, the patient is known to have, or is suspected of having non-convulsive status epilepticus. In another embodiment, the patient is known to have, or is suspected of having an epileptic seizure. In yet another embodiment, the patient is known to have, or is suspected of having a stroke.

Next, the sagittal portion 14 of the electroencephalography device is attached to the patient. In one embodiment, the patient's forehead is cleaned and dried, such as for example by wiping the patient's forehead with a gauze pad. In another embodiment, the patient's hair is parted along the midline sagittally to expose the patient's scalp, such as for example by using the end of a cotton-tipped applicator to part the hair.

Next, the forehead anchor 44 of the electroencephalography device 10 is positioned over the nasion. The release film 36 is removed from the forehead anchor 44 of the electroencephalography device 10 exposing the pre-gelled, sponge covered electrodes and the electroencephalography device is attached to the skin of the patient's forehead. Then, the remainder of the sagittal portion 14 is attached to the scalp of the patient by removing the remainder of the release film 36 and pressing it along the remainder of the sagittal portion 14 as the device is applied to the $C_Z$ location at the vertex and posteriorly to the $P_Z$, $O_1$ and $O_2$ locations on the scalp. Finally, the neck anchor 54 is attached to the base of the skull and the back of the neck.

Next, the coronal portion 12 of the electroencephalography device 10 is attached to the patient. In one embodiment, the patient's hair is parted along the central coronal plane towards the left ear, if necessary. Then, the release liner 36 covering a left side of the coronal portion 12 of the electroencephalography device is removed, and the left side of the coronal portion is attached to the patient's scalp beginning at the $C_Z$ location. Next, the left side of the coronal portion is attached to the scalp and the electrodes therein secured to the scalp along the left central plane by removing the adhesive liner toward the first ear anchor 62. Next, the release liner 36 is removed from the rear arm 66 of the first ear anchor 62 and the rear arm 66 and the electrode for the $A_1$ location are attached the mastoid behind the left ear. Then, the release liner 36 is removed from the front arm 68 of the first ear anchor 62 and the front arm 68 is attached in front of the left ear.

Next, the hair along the central coronal plane is parted towards the right ear, if necessary. Then the release liner 36 cover a right side of the coronal portion 12 of the electroencephalography device is removed and the right side of the coronal portion is attached to the patient's scalp beginning at the $C_Z$ location. Next, the right side of the coronal portion is attached to the scalp and the electrodes therein secured to the scalp along the right central plane by removing the adhesive liner toward the second ear anchor 70. Next, the release liner 36 is removed from the rear arm 74 of the second ear anchor 70 and the rear arm 74 and the electrode for the $A_2$ location are attached to the mastoid behind the right ear. Then, the release liner 36 is removed from the front arm 72 of the second ear anchor 70 and the front arm 72 is attached in front of the right ear.

In one embodiment, the electroencephalography device comprises one or more than one stabilizing strip 76 to attach the midsection 52 of the sagittal portion 14 of the electroencephalography device over the mastoid bones of the patient, and the method further comprises attaching the one or more than one strip over the mastoid bones by removing the release liner 82 on one stabilizing strip 76, parting the hair (if necessary) along the plane from $T_3$ to $O_1$, attaching the stabilizing strip 76 over the mastoid bone, attaching the stabilizing strip to the scalp toward the $O_1$ electrode site, and attaching the end of the stabilizing strip proximate to the $O_1$ electrode. Corresponding steps are performed to attach the second strip along the plane from $T_4$ to $O_2$ and attaching the end of the second strip proximate to the $O_2$ electrode.

The method then comprises mating the electroencephalography device with a reusable EEG cable suitable for use with any EEG system according to techniques well known to those with skill in the art, such as for example by connecting the connectors on the electroencephalography device to the reusable EEG interface cable and plugging the 10-20 labeled DIN connectors at the terminal end of the EEG interface cable into the appropriate 10-20 EEG head box locations.

The method then comprises using the electroencephalography device to obtain an electroencephalogram of the patients brain function. Once the electroencephalogram has been obtained, the electroencephalography device can be removed from the patient. In an embodiment, the coronal portion 12 is removed by peeling the first ear anchor 62 and the second ear anchor 70 off from around the patient's ears. The coronal portion 12 is then peeled toward the midline of the head and then back toward the back of the head to remove the coronal portion 12. The forehead anchor 44 of the sagittal portion 14 is peeled away from the patient's forehead and the sagittal portion 14 is peeled off the patient's head toward the inion.

In another embodiment of the present invention, there is provided a method of treating a disease or condition. The method comprises, first, performing electroencephalography according to the present invention. Then, the disease or condition is diagnosed. Next, the disease or condition that is diagnosed is treated. In one embodiment, the disease or condition is non-convulsive status epilepticus. In another embodiment, the disease or condition is an epileptic seizure. In yet another embodiment, the disease or condition is a stroke.

In an additional embodiment, the method further comprises treating the diagnosed disease or condition. For example, if the diagnosed disease or condition is an epileptic seizure, then treating the patient further comprises administering to the patient an anti-epilepsy drug, such as valium, ativan, midazolam, fosphenetoin, lorazepam, carbamazepine, ethosuximide, Felbatol, Gabitril, Keppra, Lamictal, Lyrica, Neorontin, Phenytoin, Topamax, Trileptal, valproate, valproic acid or Zonegran.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method of performing electroencephalography on a patient, the method comprising:
    A) providing a device for performing electroencephalography on a patient, the device comprising:
        i) a sagittal portion comprising:
            a) a forehead anchor comprising a first forehead anchor arm, an opposing second forehead anchor arm, a third forehead anchor arm between the first forehead anchor arm and the second forehead anchor arm, and an electrode set consisting of only a reference electrode, a ground electrode, and four electrodes positioned at positions F7, FP1, FP2 and F8 of the International Standard 10-20 System for electrode placement;
            b) a neck anchor comprising three arms, a first neck anchor arm, an opposing second neck anchor arm, and a third neck anchor arm between the first neck anchor arm and the second neck anchor arm; and
            c) a sagittal midsection between the forehead anchor and the neck anchor and comprising an electrode set consisting of only six electrodes positioned at positions FZ, CZ, T5, T6, O1, and O2 of the International Standard 10-20 System for electrode placement;
        ii) a coronal portion comprising:
            a) a first ear anchor comprising a front arm, a rear arm, and an electrode set consisting of only an electrode positioned at position A1 of the International Standard 10-20 System for electrode placement;
            b) a second ear anchor comprising a front arm, a rear arm, and an electrode set consisting of only an electrode positioned at position A2 of the International Standard 10-20 System for electrode placement; and
            c) a coronal midsection, between the first ear anchor and the second ear anchor, comprising an electrode set consisting of only four electrodes positioned at positions T3, C3, C4 and T4 of the International Standard 10-20 System for electrode placement;
        iii) electrical connectors electrically connecting the electrodes in the sagittal portion and the coronal portion to an electroencephalograph; and
        iv) a plurality of sponges comprising a conductive gel being attached to the electrodes; where the sagittal portion and the coronal portion each comprises a contact surface; and where the contact surfaces comprise a silicone-based adhesive, covered by a release film, for reversibly attaching the device to the patient;
    B) removing the release film from the contact surfaces exposing the silicone-based adhesive;
    C) affixing the device to the patient by affixing the forehead anchor to the forehead of the patient, affixing the sagittal midsection along a sagittal midline of the head of the patient, affixing the neck anchor to the base of the skull proximal the neck of the patient, affixing the first ear anchor around the left ear of the patient, and affixing the second ear anchor around the right ear of the patient; where affixing the device further comprises contacting the silicone-based adhesive to hair on the patient's scalp, and allowing the silicone-based adhesive to adhere to the patient's scalp; and
    D) producing an electroencephalogram.

2. The method of claim 1, wherein the contact surface of the sagittal portion extends from the forehead anchor to the neck anchor and the contact surface of the coronal portion extends from the first ear anchor to the second ear anchor.

3. The method of claim 1, where affixing the device to the patient further comprises affixing a stabilizing strip, comprising a silicone based adhesive, to the sagittal portion, the coronal portion, and the patient.

4. The method of claim 1, wherein the patient has a neurologic condition or disease.

5. The method of claim 4, further comprising diagnosing the neurologic condition or disease by interpreting the electroencephalogram.

6. The method of claim 4, further comprising treating the neurologic condition or disease that is diagnosed.

7. The method of claim 4, where the neurologic condition or disease is non-convulsive status epilepticus.

8. The method of claim 4, where the neurologic condition or disease is an epileptic seizure.

9. The method of claim 4, where the neurologic condition or disease is a stroke.

10. The method of claim 1, wherein affixing the device to the patient further comprises:
    affixing a first stabilizing strip, comprising a silicone based adhesive, to the sagittal midsection at position T3, the coronal portion at position T5, and the patient; and
    affixing a second stabilizing strip, comprising a silicone based adhesive, to the sagittal midsection at position T4, the coronal portion at position T6, and the patient.

* * * * *